United States Patent [19]

Kresken et al.

[11] Patent Number: 5,026,690

[45] Date of Patent: Jun. 25, 1991

[54] ANTIVIRAL AGENT

[75] Inventors: Joachim Kresken, Krefeld Forstwald; Bernd Komp, Seligenstadt; Dolf Stockhausen, Krefeld, all of Fed. Rep. of Germany

[73] Assignee: Chemische Fabrik Stockhausen GmbH, Krefeld, Fed. Rep. of Germany

[21] Appl. No.: 299,916

[22] PCT Filed: Jul. 30, 1987

[86] PCT No.: PCT/EP87/00417

§ 371 Date: Dec. 28, 1988

§ 102(e) Date: Dec. 28, 1988

[87] PCT Pub. No.: WO88/00828

PCT Pub. Date: Feb. 11, 1988

[30] Foreign Application Priority Data

Aug. 2, 1986 [DE] Fed. Rep. of Germany ....... 3626309

[51] Int. Cl.$^5$ ..................... A01N 51/00; A01N 41/06
[52] U.S. Cl. ...................................... 514/155; 514/604
[58] Field of Search ................................ 514/155, 604

[56] References Cited

U.S. PATENT DOCUMENTS

| | | | |
|---|---|---|---|
| 3,034,955 | 5/1962 | Frick | 167/37 |
| 4,034,110 | 7/1977 | Mitrovic | 424/311 |
| 4,870,107 | 9/1989 | Yoshimoto | 514/604 |

OTHER PUBLICATIONS

Banthell, E., CA 107:197789w, 1987.
Schmid, Otto, CA 84:150378c, 1976.

Primary Examiner—Stanley J. Friedman
Assistant Examiner—Russell Travers
Attorney, Agent, or Firm—Sprung Horn Kramer & Woods

[57] ABSTRACT

The present invention relates to the use of sulphonamide derivatives for the treatment of diseases caused by viruses, especially caused by enclosed viruses such as, e.g., herpes simplex, as well as to an antiviral agent having a content of these sulphonamide derivatives as active substance, optionally together with pharmaceutically acceptable carriers and/or auxiliaries.

3 Claims, No Drawings

ANTIVIRAL AGENT

The invention relates to an antiviral agent, especially for measures against enclosed viruses, such as herpes viruses, having a content of sulphonamide derivatives of 4,4'-diaminostilbene disulphonic acid-2,2', and/or of 4,4'-diaminodiphenylethane disulphonic acid-2,2', the use of these derivatives for the treatment and prevention of virus diseases, especially of diseases caused by enclosed viruses, such as herpes virus, as well as the use of these derivatives for the preparation of an antiviral agent.

Such sulphonamide derivatives of the general formula

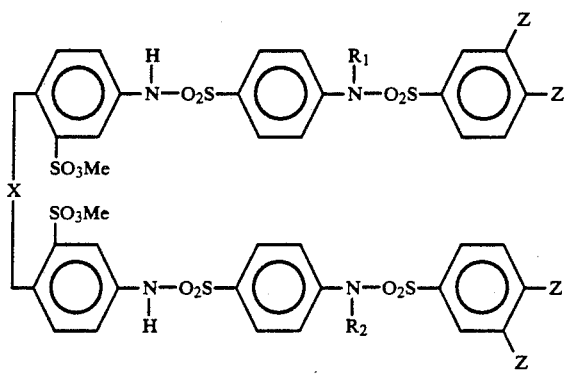

wherein X represents the group —CH=CH— or —CH$_2$—CH$_2$—, Z represents chlorine or bromine, Me represents a non-toxic cation, preferably alkali or ammonium, and R$_1$ and R$_2$ which may be the same or different represent hydrogen or the 3,4-dihalogenobenzene sulphonyl group are known from DE-PS 24 33 723. These products absorb radiation (especially UV-radiation), have a protein coagulating effect, and are used as active substance in skin protecting agents.

These sulphonamide derivatives which derive from the 4,4'-diaminostilbene disulphonic acid-2,2' and its analogon with the stilbene double-bond being hydrogenated, the 4,4'-diaminodiphenyleth disulphonic acid-2,2', are produced by condensation of the starting products 4,4'-diaminostilbene disulphonic acid-2,2' or 4,4'-diaminodiphenylethane disulphonic acid-2,2' in the form of their salts or their N,N'-monosubstituted derivatives in aqueous solution either with 1-chlorosulphonyl-4-acetaminobenzene or with 1-chlorosulphonyl-4-carbethoxi aminobenzene respectively the N-substituted derivatives of these compounds, subsequent deliberation of the terminal primary or secondary amino group by hydrolysis and final reaction of these saponification products with 1-chlorosulphonyl-3,4-dihalogenobenzene, preferably with 3,4-dichlorobenzene sulphonyl chloride. It is preferred to use for the reaction the water-soluble salts of the starting products, especially the calcium or sodium salts. The final products in which Me represents a non-toxic cation, preferably alkali, such as sodium or ammonium, are received, if necessary, from the soluble salts with other cations (e.g.,the calcium salts) by reacting with sodium carbonate, -bicarbonate or ammonium oxalate.

Surprisingly, it has been found that the above mentioned sulphonamide derivatives have a high virucidal and antiviral effect, especially against viruses provided with an enclosure, further called "enclosed" viruses, without evolving cytotoxic side effects.

Typical examples of such "enclosed" viruses are the herpes viruses, especially herpes simplex, but the varicella zoster viruses as well.

On the basis of the therapy measures today available, diseases caused by herpes simplex viruses, such as herpes labialis and herpes genitalis, can be treated only with very unsatisfying results (Wassilew Sawko W., Möglichkeiten und Grenzen der Chemotherapie bei Erkrankungen durch das Herpes-simplex- und Varicella-Zoster-Virus, Der Hautarzt, 34, 1 to 5, (1983); Wassilew, Sawko W., Virustatika in der Dermatologie Der Hautarzt, 37, 259–262, (1986), Ring, J., Fröhlich, H.H., Wirkstoffe in der dermatologischen Therapie, 140 to 143, Springer Verlag (1985)).

Most of the products used so far, proved to be ineffective or showed unacceptable side effects in clinical studies. Primarily these side effects are toxic influences on the host cell affected by the virus, but as well, e.g., the initiation of allergies (see Wassilew, Sawko, indicated above).

Thus the object of the invention is the preparation of an effective antiviral agent which is suitable especially for the treatment and prevention of diseases caused by enclosed viruses, such as herpes simplex viruses of type 1 and 2, and which shows no, or at least negligible side effects This object is achieved by an agent containing as active substance the sulphonamide derivatives mentioned in the beginning. In other words, the object is achieved by using the a.m. special sulphonamide derivatives for the treatment of viruses, especially of enclosed viruses, such as herpes viruses, as well as by using these effective compounds for the production of an suitable antiviral agent The products used according to the present invention are applied in pharmaceutical preparations in a concentration of 0.1 to 20% (% wt.), optionally together with pharmaceutically acceptable carriers diluting agents and/or auxiliaries. The carrier agents and auxiliaries respectively are substances known in the galenics; water, lower mono or multivalent alcohols, such as glycerol, and paraffin oil or vaseline, may be used as carriers and as diluting agents respectively. Thus, the products according to the present invention may be used in all known pharmaceutical forms of administration. The topical use, e.g., as cream, ointment, paste, gel or solvent, is preferred.

However, the sulphonamide derivatives mentioned above may not only be used for therapeutical purposes, but also in cosmetics, such as, e.g., lipsticks, feminine hygiene products, or special skin protection products, in the infection prophylaxis, and prevention against further spread of the viruses. Furthermore, they can be used as additives in skin cleaning agents, such as soaps, or in combination with disinfectants.

The compounds according to the present invention show an inhibition of the virus titre of up to 99.999% in test concentrations of 25 to 100 μg/ml at single-layer cell cultures of kidney cells (ape) inoculated with herpes simplex viruses. A toxic influence on the host cell only occurs at a concentration from about 250 μg/ml upwards.

In contrast to the products used according to the invention most of the antiviral agents known so far, either have an insufficient inhibitory effect or, if the effect is sufficient, they have a significant toxic effect on the host cell, measured by its protein synthesis capability.

It is especially advantageous that the inventive products show an extra-cellular virucidal effect which makes possible the use as disinfectant and—as mentioned above—in the prophylaxis.

The extra-cellular virucidal effect is achieved by a damage of the virus membrane, which can be reconstructed by the electron microscope, thus the viruses loose their infectiousness.

In order to record the virucidal effect quantitively, the herpes simplex viruses at first are incubated with the compound according to the present invention. Subsequent to this, the remaining infectiousness on the host cells is determined.

Both antiviral and virucidal efficiency of the products used according to the present invention, determined by the end point titration method, lead to a decrease of the initial virus titer of up to 99.999% for herpes simplex viruses by the use of the effective compound.

The efficiency of the products used according to the present invention is shown as well in an in-vivo-model with white mice. In this test the animals are treated with the compounds to be tested, which are prepared, e.g., as a solution or cream, either before or after an infection with herpes simplex viruses in their back.

EXPERIMENTAL WORK

A. Production of the active substances 185 g (0.5 mole) of 4,4'-diaminostilbene disulphonic acid-2,2' are added to 1100 ml of water heated to 60–65° C. and neutralized with about 84.5 g (0.95 mole) of a 45% sodium hydroxide solution so that the pH-value of the solution is not increased above 6.5. As soon as a clear solution is formed, 246 g (1.05 mole) of powdery p-acetaminobenzenesulphonyl chloride is added with stirring over a period of two hours in such a way that at a temperature of 60–65° C. the pH-value of the solution can be kept in a range of 5.5 to 6.5 by simultaneous addition of about 510 g of a 9% sodium hydroxide solution (1.1 mole). Hereby, partial precipitation of the condensation product may occur. About 240 g of a 45% sodium hydroxide solution (2.7 mole) is added subsequently, in order to saponify the acetyl group, and the reaction mixture is refluxed for two hours; whereby a pH-value of above 11 should be kept.

For purification purposes the reaction product is precipitated with 200 g of a 30% hydrochloric acid (1.6 mole). At first, the solution is set to a pH-value of about 9 with a portion of the hydrochloric acid and filtered in hot condition. The remaining portion of the hydrochloric acid is then added to the clear filtrate at a temperature of 80–85° C. whereby the pH-value should not fall below 6. After cooling to 30–40° C. the precipitated product is filtered by suction, washed thoroughly and sucked off rigorously. The moist, granular, yellowy product may either be dried or processed directly.

The product is obtained in nearly quantitive yield with high purity and identified by IR-spectroscopy, N- and S-determination in combination with the alkali titration equivalent and by thin-layer chromatography.

0.5 mole (362 g as dry substance) of the intermediate product described above are added to 2615 ml of water with simultaneous heating. As soon as a temperature of 90–95° C. is reached, 66.8 g of a 45% sodium hydroxide solution (0.75 mole) is added, whereby a pH-value of 8.3 to 8.4 is to be kept and a temperature of 62 to 65° is adjusted. 306.5 g (1.25 mole) of 3,4-dichlorobenzene sulphonyl chloride is added smoothly to the now clear solution with keeping a reaction temperature of 62–65° C. up to a pH-value of 5.5, while the pH-value of the solution is controlled carefully by adding a 9% sodium hydroxide solution. Then the pH-value is increased to 8.0 with sodium hydroxide solution and kept at this pH-value by simultaneously adding further 122.5 g (0.5 mole) of 3,4-dichlorobenzene sulphonyl chloride and a 9% sodium hydroxide solution. The total consumption of the 9% sodium hydroxide solution is about 711 g. The sulphonyl chloride is added within about 2 hours. After termination of the condensation it is stirred at a temperature of 60–65° C. for ½ hour, until the pH-value remains constant at 6.2 to 6.4.

For purification purposes the condensation product is precipitated with strong stirring at 90–95° C. by acidification with 357 g of a 30% hydrochloric acid (2.94 mole). The pH-value of the supernatant solution is below 1. The precipitated sulphonamide is sucked off for further purification and again dissolved in 2980 ml of water under neutralization with about 180 g of a 9% sodium hydroxide solution. The pH-value of the resulting solution is 6–6.5.

In order to separate water-insoluble by-products, the solution is extracted four times with 125 ml trichloroethylene each, removing at the end the residual content of trichloroethylene by vacuum distillation at 98–99° C. or by distillation at normal pressure at 110° C. A syrup-like, gelatinous, amber-coloured and clear liquid with a content of 12 to 15% active substance is received which may be used as it is or which may be converted into a powdery solid by a suitable drying method, such as, e.g., in a drying oven, by spray drying or freeze drying. The identification of the reaction product is carried out by thin-layer chromatography.

B. In Vitro-tests

Determination of the antiviral and virucidal effect

Material and Methods

For the following research, solutions of the above described substances were produced in water or in DMSO/water-mixtures and diluted to 4 different test concentrations (100, 75, 50, and 25 ug/ml) with nutrient medium or isotonic phosphate buffer.

(a) Antiviral Efficiency

Starting from a suspension of herpes simplex viruses (type 1 or 2) in nutrient medium (TCD$_{50}$/ml: $10^6$), seven solutions with dilutions differing by factor 10 were prepared (TCD$_{50}$/ml:$10^5$-$10^{-1}$). Monolayers of VERO-cells were infected on microtiter plates with 0.1 ml of each of these dilutions, and incubated for 90 minutes at 37° C. Then 0.1 ml of the 4 concentrations of the test compounds were added to each of the different virus concentrations.

The plates were incubated at 37° C. in a wetting incubator for 5 days. A cytotoxity-, cell-, and virus control was carried out in parallel for each concentration ratio. The cytopathogenic effect on the mono layers was observed daily.

(b) Virucidal efficiency

The same volumes of the 4 concentrations of the compounds to be tested were incubated with a suspension of herpes-simplex viruses (type 1 or 2, TCD$_{50}$/ml:10$^5$) for 1 hour at 37° C. Then 7 solutions diluted by the factor 10 each were produced from the 4 starting suspensions. 0.2 ml of these solutions were each put into microtitre plates charged with monolayers of VERO-cells, in order to determine the still remaining virus titre. The plates were incubated at 37° C. in a wetting incubator for 5 days. Furthermore, a blank (without test compound) was run. The cytopathogenic effect was observed daily.

Test results

The antiviral and virucidal effect of the compounds tested is expressed as reduction factor by which the initial virus titre has been reduced.

The following table 1 shows the antiviral and virucidal effect on herpes simples viruses of type 1 or 2; the same concentrations of active substance were used.

TABLE 1

Results of the in-vitro tests

| Substance/ concentration | | antiviral effect (expressed as reduction factor) | virucidal effect (expressed in reduction factor) |
|---|---|---|---|
| Active substance according to the invention | 100 μg/ml | $10^4$–$10^5$ | $10^4$–$10^5$ |
| Active substance according to the invention | 75 μg/ml | $10^3$–$10^4$ | $10^3$–$10^4$ |
| Active substance according to the invention | 50 μg/ml | $10^2$–$10^3$ | $10^2$–$10^3$ |
| Active substance according to the invention | 25 μg/ml | $10$–$10^2$ | $10$–$10^2$ |

The intervals indicated result from different preparations of the test concentrations and the deviations in solubility resulting therefrom.

The substances do not cause morphological modifications of the cells with the tested concentrations.

C. In vivo-tests

Material and Methods

Mice of the type Mus Musculus Mutand gene type HR/HR (aged 3 weeks) were divided into groups of 8-12 animals each, and infected with 100 μl of a suspension of herpes simplex viruses type 1 or 2 (10$^6$ TCD$_{50}$/ml) each.

The treatment of the animals was carried out according to different methods:

Method of treatment a: treatment 48, 24, and 1.5 hours before this infection.

Method of treatment b: treatment 1.5 hours after the infection and then twice per day over a period of 10 days.

The test results are summarized in the following table.

TABLE 2

Results of the in vivo-tests

| Substance/ concentration | Vehicle | Method of treatment | Clinical results (% of test animals having normal herpes lesions*) |
|---|---|---|---|
| Substance according to the invention | 2% DMSO/water (30:70) | a | 0 |
| Substance according to the invention | 2% DMSO/water (30:70) | b | 75 |
| Substance according to the invention | 5% DMSO/water (30:70) | a | 5 |
| Substance according to the invention | 5% DMSO/water (30:70) | b | 80 |
| Substance according to the invention | 1% water | a | 0 |
| Substance according to the invention | 10% o/w-cream | a | 16 |
| Substance according to the invention | 10% o/w-cream | b | 88 |
| Control without active substance | — DMSO/water (30:70) | a | 100 |
| Control without active substance | — DMSO/water (30:70) | b | 100 |

*Within 3 to 4 days after the infection, small, white nodules occur which develop to characteristic herpes lesions after further 6 to 7 days.

We claim:

1. A method of combating a virus infection in a patient in need thereof which comprises administering to said patient an antivirally effective amount of a sulphonamide of the formula

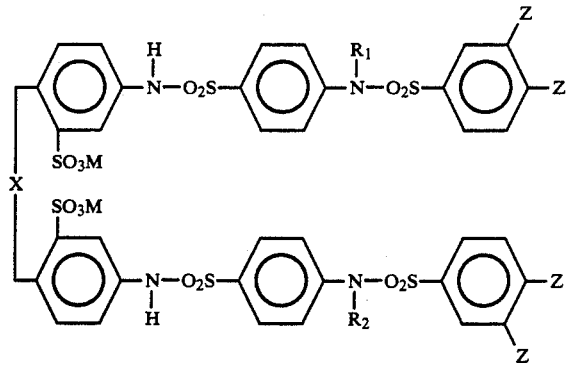

wherein
X represents the group —CH=CH— or —CH$_2$—CH$_2$—,
Z represents chlorine or bromine,
M represents a non-toxic cation, and
R$^1$ and R$^2$ each independently represent hydrogen of 3,4-dihalogenobenzene sulphonyl group.

2. The method according to claim 1, wherein the virus infection being combatted is Herpes simplex.

3. The method according to claim 1, wherein at least one of R$_1$ and R$_2$ is a 3,4-dihalogenobenzene sulphonyl group.

* * * * *